(12) United States Patent
Sheydin

(10) Patent No.: US 10,369,043 B2
(45) Date of Patent: Aug. 6, 2019

(54) MULTI-LAYER HEATING MAT FOR PROVIDING THERAPEUTIC HEAT TO AN AREA OF THE BODY

(71) Applicant: Mikhail Sheydin, Brooklyn, NY (US)

(72) Inventor: Mikhail Sheydin, Brooklyn, NY (US)

( * ) Notice: Subject to any disclaimer, the term of this patent is extended or adjusted under 35 U.S.C. 154(b) by 161 days.

(21) Appl. No.: 15/474,015

(22) Filed: Mar. 30, 2017

(65) Prior Publication Data

US 2018/0071140 A1 Mar. 15, 2018

Related U.S. Application Data

(63) Continuation-in-part of application No. 29/581,727, filed on Oct. 21, 2016, now abandoned, and a continuation-in-part of application No. 29/581,786, filed on Oct. 21, 2016, now abandoned, and a continuation-in-part of application No. 29/581,733, filed on Oct. 21, 2016, now abandoned.

(60) Provisional application No. 62/393,334, filed on Sep. 12, 2016.

(51) Int. Cl.
*A61F 7/08* (2006.01)
*A61N 5/06* (2006.01)
*A61F 7/00* (2006.01)

(52) U.S. Cl.
CPC ............... *A61F 7/08* (2013.01); *A61F 7/007* (2013.01); *A61N 5/0625* (2013.01); *A61F 2007/0052* (2013.01); *A61F 2007/0071* (2013.01); *A61F 2007/0086* (2013.01); *A61F 2007/0088* (2013.01); *A61F 2007/0094* (2013.01); *A61F 2007/0096* (2013.01); *A61N 2005/0626* (2013.01); *A61N 2005/0643* (2013.01); *A61N 2005/0659* (2013.01)

(58) Field of Classification Search
CPC .............................. A61N 2/00–02; A61F 7/08
See application file for complete search history.

(56) References Cited

U.S. PATENT DOCUMENTS

2004/0158176 A1* 8/2004 Park ................... A61H 15/0078
601/18

OTHER PUBLICATIONS

Purple Medicrystal Amethyst Agate Bio-Magnetic Photon Mat Midsize (pdf file attached), dated Sep. 30, 2016, retrieved on Nov. 1, 2018 (Year: 2016).*

(Continued)

*Primary Examiner* — Thaddeus B Cox

(57) ABSTRACT

A heating mat that, by making use of a multilayered structure, is able to provide therapeutic benefits to a user. The heating mat has a waterproof base layer, a heating layer, PEMF emitters, and a primary therapeutic layer. The primary therapeutic layer uses therapeutic stones and a stone harness to maintain the therapeutic stones in a position that facilitates treatment. The waterproof base layer is a water-impervious membrane that prevents external fluids from damaging the electronic components of the heating mat. The heating layer functions as a flexible heating element for the heating mat and is mounted across the waterproof base layer. The PEMF emitters are devices which generate pulses of EM energy that are known to have therapeutic properties. The PEMF emitters are mounted in between the waterproof base and the heating layer. The primary therapeutic layer is mounted across the heating layer, opposite to the waterproof base layer.

12 Claims, 5 Drawing Sheets

(56) References Cited

OTHER PUBLICATIONS https://web.archive.org/web/20161029193159/http://medicrystal.com/assets/pdf/MediCrystal_catalog.pdf (Year: 2016).*
https://web.archive.org/web/20170103071619/https://healthyline.com/product/tao7224p/ (Year: 2017).*
https://healthyline.com/wp-content/uploads/2016/11/Inframat-Pro-Layers.png (Year: 2016).*

* cited by examiner

MULTI-LAYER HEATING MAT FOR PROVIDING THERAPEUTIC HEAT TO AN AREA OF THE BODY The current application claims a priority to the U.S. Provisional Patent application Ser. No. 62/393,334 filed on Sep. 12, 2016.

FIELD OF THE INVENTION

The present invention relates generally to a therapeutic heating mat. More specifically, the present invention relates to a heating mat that makes use of the therapeutic properties of precious stones to benefit a user.

BACKGROUND OF THE INVENTION

Traditional heating mats function as multipurpose devices. A single heating mat can be employed to warm a user on a cold night. The same heating mat could be used as a therapeutic aid for stiff or sore muscles. Well-designed heating mats can even be incorporated into pillows and seat cushions. These devices are useful, yet they can be improved upon.

The present invention, the multi-layer heating mat for providing therapeutic heat to an area of the body, combines the functionality of the heating mat with the therapeutic benefits that can be gained from precious stones, semi-precious stones, and naturally semi-conductive gemstones. When such stones are exposed to the heat of the heating mat, the stones generate infrared and near infrared radiation. The present invention can be applied to any part of the user's body that requires treatment. In addition to precious stones, the present invention employs pulse electromagnetic field (PEMF) emitters to generate EM fields that facilitate healing. The present invention, is designed to address many types of ailments. As such, the present invention makes use of multiple layers of materials known for their therapeutic properties. Finally, the present invention is designed to function as an aesthetically pleasing device and can be covered with various types of fabrics and cushions without losing therapeutic functionality.

DETAIL DESCRIPTIONS OF THE INVENTION

All illustrations of the drawings are for the purpose of describing selected versions of the present invention and are not intended to limit the scope of the present invention.

In reference to FIG. 1 through FIG. 5, the present invention is a heating pad that makes use of therapeutic stones and PEMF emitters to produce infrared and negative ion waves. To accomplish this, the present invention is designed as a pad made by stacking multiple layers of materials that work in concert to augment the therapeutic capabilities of a traditional heating pad. The term "therapeutic stones" is used herein to refer to gemstones and minerals including, but not limited to, amethyst, jade, and tourmaline. The therapeutic stones used in the present invention emit infrared waves and negative ion waves when heated. These emissions are coupled with the electromagnetic fields generated by the PEMF emitters to facilitate health and wellness. The arrangement of the layers of material used in the present invention is designed to provide a therapeutic benefit while reducing any negative effects of traditional heating pads. To that end, the present invention comprises a waterproof base layer 1, a heating layer 2, a plurality of PEMF emitters 5, and a primary therapeutic layer 6. These components are stacked on top of each other to create a flexible apparatus that has uses including, but not limited to, blankets, pillows, cushions, and upholstery covers.

Figure 1:
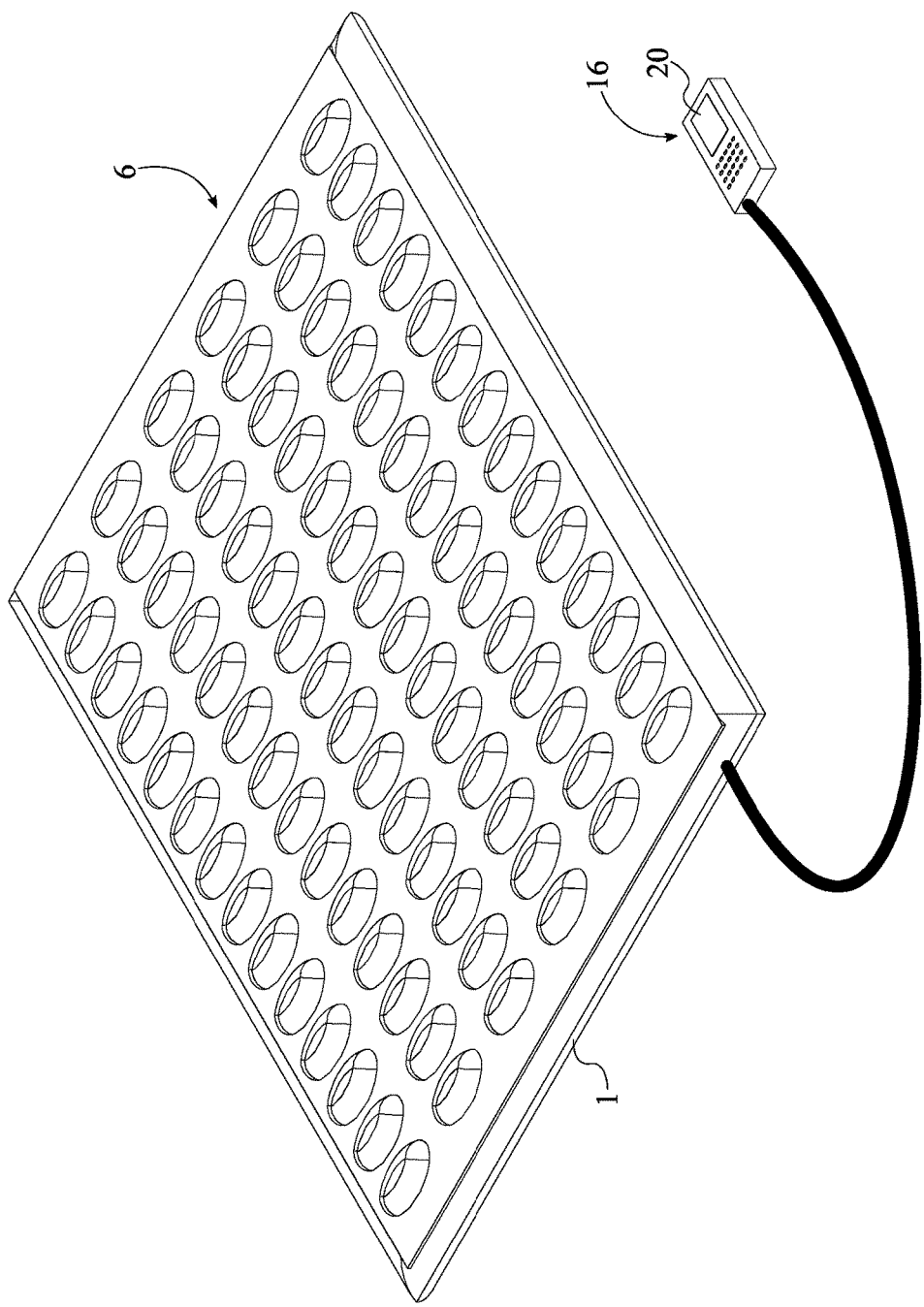
FIG. 1 is a perspective view of the present invention.
Figure 2:
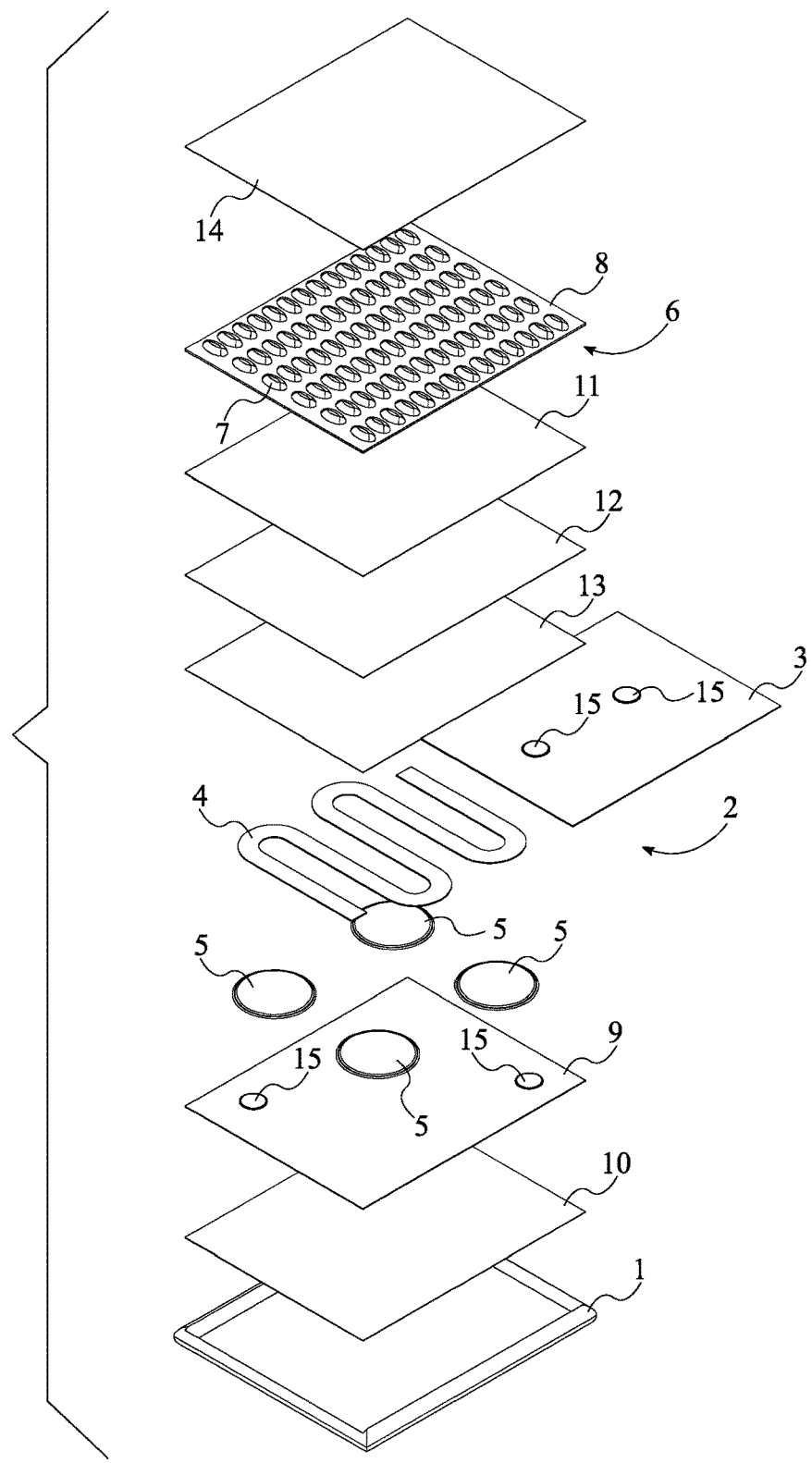
FIG. 2 is an exploded perspective view of the present invention without the user controller.
Figure 3:
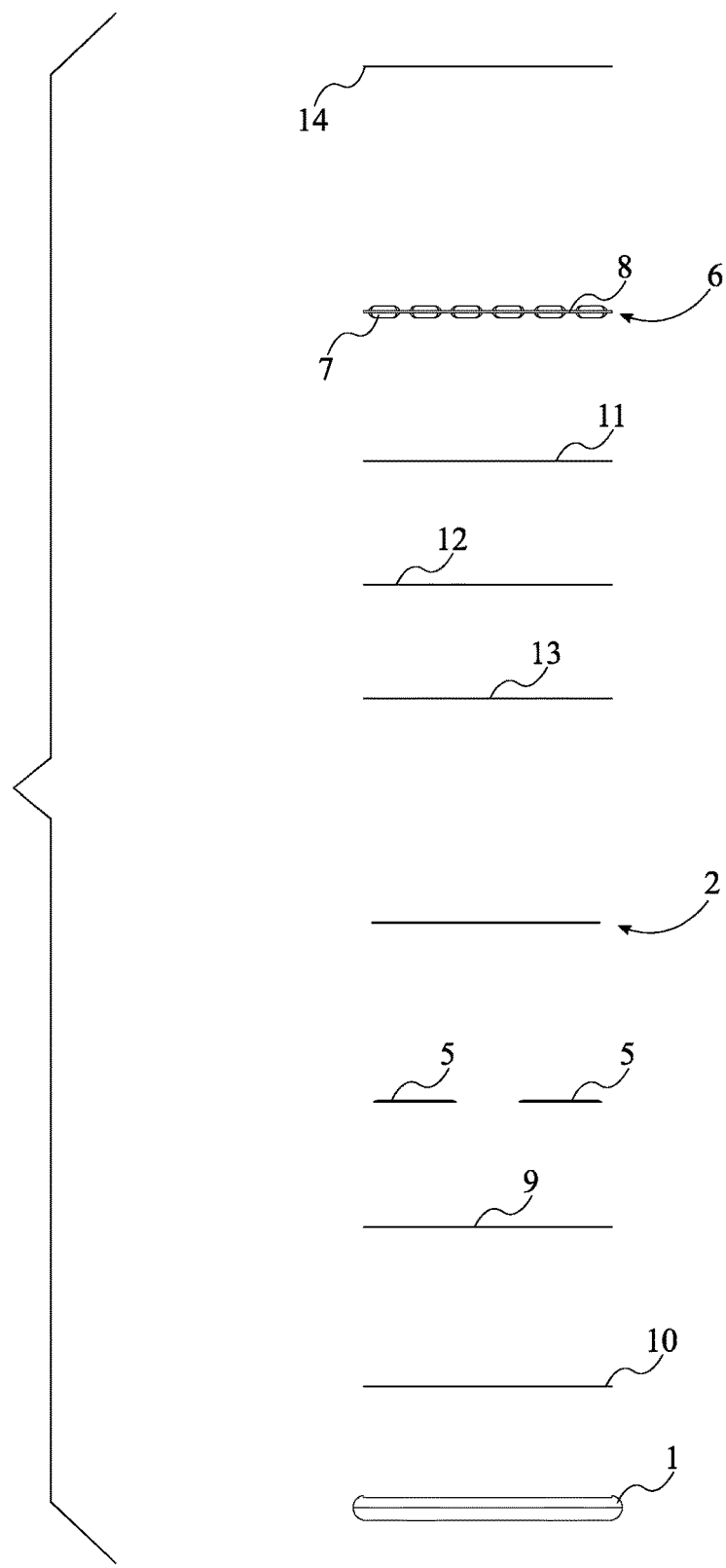
FIG. 3 is an exploded front view of the present invention without the user controller.

In reference to FIG. 2, each of the layers of the present invention is a flexible sheet that is designed to serve a unique function as part of a flexible heating pad. The primary therapeutic layer 6 is a flexible sheet that has embedded therapeutic stones. Specifically, the primary therapeutic layer 6 comprises a plurality of therapeutic stones 7 and a stone harness 8. In the present invention, the waterproof base layer 1 is a flexible membrane of waterproof material that is used to prevent fluids from passing through the present invention. Additionally, the waterproof base layer 1 forms the foundational layer onto which the remaining layers of are mounted. The heating layer 2 is a flexible sheet with integrated heating elements. The heating layer 2 is mounted across the waterproof base layer 1 so that the heating layer 2 does not short-circuit from any liquids that could potentially be surround the present invention. Each of the plurality of PEMF emitters 5 is an electronic device that produces intermittent pulses of electromagnetic fields. In the preferred embodiment of the present invention, the plurality of PEMF emitters 5 is mounted in between the waterproof base layer 1 and the heating layer 2. Consequently, the position of the plurality of PEMF emitters 5 is designed to optimize the therapeutic benefits gained from using the present invention. In an alternative embodiment of the present invention, the plurality of PEMF emitters 5 is distributed across multiple layers. The primary therapeutic layer 6 is mounted across the heating layer 2, opposite to the waterproof base layer 1. As a result, the therapeutic layer 2 is mounted in a position that enables the heating layer 2 to transfer heat to the plurality of therapeutic stones 7. The stone harness 8, is the sheet of material into which the plurality of therapeutic stones 7 is embedded. Specifically, the plurality of therapeutic stones 7 is mounted onto the heating layer 2 by the stone harness 8. Thus mounted, the plurality of therapeutic stones 7 is retained in a position that facilitate therapeutic benefits and aesthetic appeal.

In reference to FIG. 2, the heating layer 2 is able to function as a single flexible sheet by housing a heating element within a flexible envelop of material. To accomplish this, the heating layer 2 comprises a sheath 3 and a heating element 4. The sheath 3 is an envelope of flexible material that is used to house the heating element 4. The heating element 4 is a flexible device used to transform electrical energy into thermal energy. The heating element 4 is enveloped by the sheath 3. Accordingly, the sheath 3 maintains the heating element 4 in a desired position within the present invention. For example, the sheath is a fabric pouch into which the heating element 4 is inserted. The heating element 4 is preferably a flexible cable that generates heat when an electrical current is supplied.

The present invention further comprises a heat-shielding layer 9. The heat-shielding layer 9 is a sheet of material designed to prevent the transference of thermal energy. Additionally, the heat-shielding layer 9 is mounted in between the waterproof base layer 1 and the heating layer 2. This location enables the heat-shielding layer 9 to limit the transference of heat to the surface on which the present invention rests. In the preferred embodiment of the present invention, the heat-shielding layer 9 is made of aluminum sheeting. The material of the heat-shielding layer 9 can be, but is not limited to, steel, composite materials, or ceramic insulation.

In reference to FIG. 2, to add shape, the present invention further comprises a semi-rigid material layer 10. The semi-rigid material layer 10 is mounted in between the waterproof base layer 1 and the plurality of PEMF emitters 5. Consequently, the semi-rigid material layer 10 enables the present invention to function as a blanket without being deformed in a manner that damages the electrical components inside. The semi-rigid material layer 10 is preferably made of pressed cotton. The semi-rigid material layer 10 can be made of, but is not limited to, plastic, rubber, or natural fibers.

In reference to FIG. 2, the present invention further comprises a heat-distribution layer 11. The heat-distribution layer 11 is mounted in between the heating layer 2 and the primary therapeutic layer 6. As a result, the heat-distribution layer 11 evenly distributes the heat generated by the heating layer 2 across the underside of the primary therapeutic layer 6.

In reference to FIG. 2, the homeopathic benefits gained by use of the present invention are the result of a combination of three primary factors, heat transmission, PEMF absorption, and the emissions generated by the plurality of therapeutic stones 7. To that end, the plurality of therapeutic stones 7 is made of at least one material selected from the group consisting of: amethyst, jade, and tourmaline. The homeopathic benefit gained from using these stones increases the present invention's therapeutic effectiveness. The plurality of therapeutic stones 7 can include stones such as, but not limited to, citrine, opal, calcite, and ruby.

In reference to FIG. 2, the present invention further comprises an EMF-filtering layer 12. The EMF-filtering layer 12 is a sheet of material designed to prevent the transmission of harmful EMF energy. To that end, the EMF-filtering layer 12 is mounted in between the heating layer 2 and the primary therapeutic layer 6. Thus mounted, the EMF-filtering layer 12 prevents any unwanted EMF energy from passing into the therapeutic stones layer while permitting the transmission of the EMF output from the plurality of PEMF emitters 5. Preferably, the EMF-filtering layer 12 is made from copper. In a supplementary embodiment, the EMF-filtering layer 12 is made from a material that prevents the transmission of EMF energy.

In reference to FIG. 2, the present invention further comprises a secondary therapeutic layer 13. The secondary therapeutic layer 13 is a layer of homeopathic material that is mounted in between the heating layer 2 and the primary therapeutic layer 6. Accordingly, the secondary therapeutic layer 13 augments the homeopathic benefits of the primary therapeutic layer 6. The secondary therapeutic layer 13 is preferably made from a material selected from the group consisting of: bamboo, carbon fiber material, and charcoal.

In reference to FIG. 2, the present invention further comprises a protective shell layer 14 which is a piece of material that provides aesthetic appeal. The protective shell layer 14 is mounted across the primary therapeutic layer 6, opposite to the heating layer 2 so that the protective shell layer 14 is able to prevent the primary therapeutic layer 2 from being scratched by an external object.

In reference to FIG. 2, the present invention further comprises at least one temperature sensor 15 and a microcontroller 18. The at least one temperature sensor 15 is an electronic temperature sensor that generates an electronic reading of the temperature of the present invention. To that end, the at least one temperature sensor 15 is in thermal communication with the heating layer 2. Consequently, the at least one temperature sensor 15 is used to measure the temperature inside the present invention. The microcontroller 18 is a processing device capable of communicating with and controlling the other electronic components of the present invention. As such, the at least one temperature sensor 15 is electronically connected to the microcontroller 18. As a result, the electronic readings of the at least one temperature sensor 15 are transferred to the microcontroller 18. The Microcontroller uses this information to alert the user of the temperature of the heating layer 2. Additionally, the temperature data is used by the microcontroller 18 to adjust the temperature of the heating layer 2.

Figure 4:
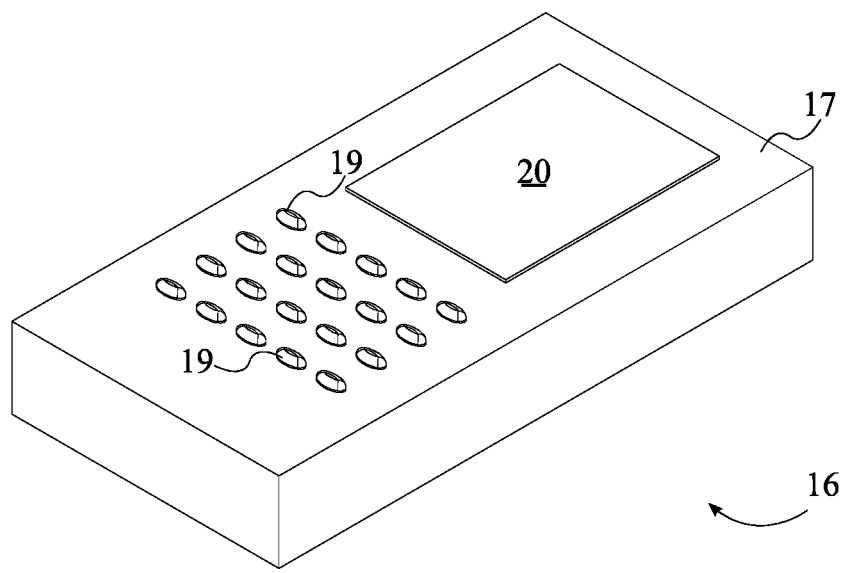
FIG. 4 is a perspective view of the user controller for the present invention.
Figure 5:
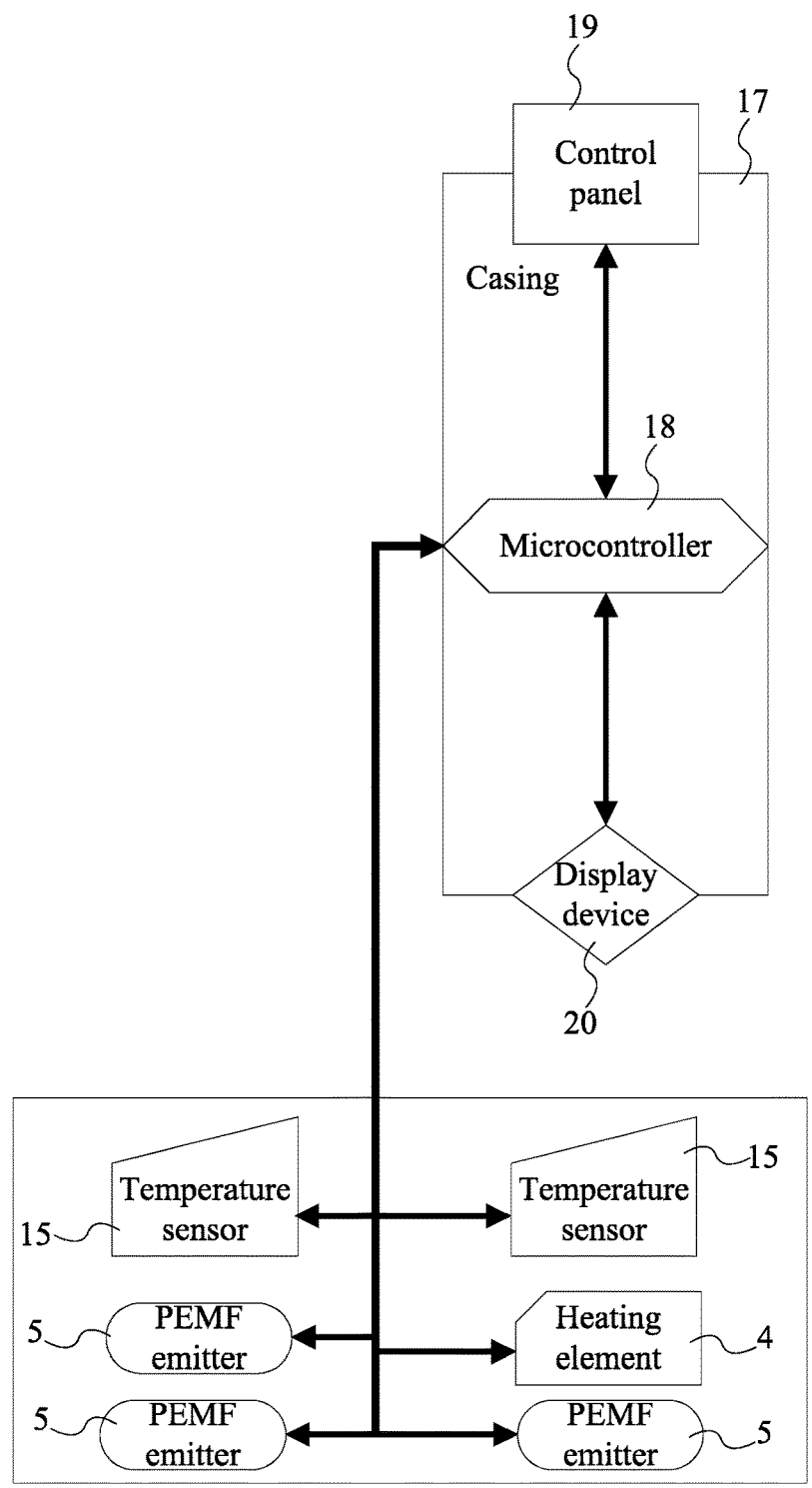
FIG. 5 is a schematic of the electronic components for the present invention.

In reference to FIG. 2 and FIG. 4, the present invention further comprises the user controller 16. The user controller 16 is a user interface device that comprises a casing 17, a microcontroller 18, and a control panel 19. The casing 17 is an ergonomically shaped enclosure that is intended to fit into the hand of the user. The control panel 19 is a user interface that enables the user to monitor and modify the electrical state of the present invention. The control panel 19 is externally mounted onto the casing 17. Thus mounted, the control panel 19 facilities manipulation by the user's hands. The control panel 19 can be any combination of user-interface devices including, but not limited to, touchscreen displays, buttons, joysticks, and dials. The microcontroller 18 is mounted within the casing 17. Accordingly, the casing 17 functions as a housing protecting the microcontroller 18. The microcontroller 18 is electronically connected to the control panel 19, the heating layer 2, and the plurality of PEMF emitters 5. Consequently, the microcontroller 18 is able to dictate the function of these components. The microcontroller 18 is able to dictate the magnitude and frequency of the plurality of PEMF emitters 5. The electronic connection with the microcontroller 18 enables the microcontroller 18 to modify the temperature of the heating layer 2. Additionally, the microcontroller 18 interprets any data transmitted by the electronic components of the present invention. This enables the microcontroller 18 to output this system information to the user through the control panel 19. The user controller 16 further comprises a display device 20. The display device 20 is an electronic component for visually relaying information to the user. The display device 20 is externally mounted onto the casing 17, offset from the control panel 19. As a result, the display device 20 is maintained in a position that facilitates visual inspection by the user. The microcontroller 18 is electronically connected to the display device 20 so that the display device 20 is able to present the user with information about the state of the present invention.

Although the invention has been explained in relation to its preferred embodiment, it is to be understood that many other possible modifications and variations can be made without departing from the spirit and scope of the invention as hereinafter claimed.

What is claimed is:

1. A multi-layer heating mat for providing therapeutic heat to an area of a body comprising:
   a heating layer;
   a plurality of pulse electromagnetic field (PEMF) emitters;

a primary therapeutic layer;
the primary therapeutic layer comprising a plurality of therapeutic stones;
the primary therapeutic layer being located above the heating layer;
the plurality of therapeutic stones being configured to emit infrared waves and negative ions in response to the plurality of therapeutic stones being heated by the heating layer; and
the multi-layer heating mat being configured to be used as a flat unit or a wearable unit.

2. The multi-layer heating mat as claimed in claim 1 comprising:
the heating layer comprising a sheath and a heating element; and
the heating element being enveloped by the sheath.

3. The multi-layer heating mat as claimed in claim 1 comprising:
a protective shell layer;
a heat-distribution layer;
an EMF-filtering layer;
a secondary therapeutic layer;
a heat-shielding layer;
a semi-rigid material layer;
a waterproof layer;
the semi-rigid material layer being located above the waterproof layer;
the heat-shielding layer being located above the semi-rigid material layer;
the plurality of pulse electromagnetic field (PEMF) emitters being located above the heat-shielding layer;
the heating layer being located above the plurality of pulse electromagnetic field (PEMF) emitters;
the secondary therapeutic layer being located above the heating layer;
the EMF-filtering layer being located above the secondary therapeutic layer;
the heat-distribution layer being located above the EMF-filtering layer;
the primary therapeutic layer being located above the heat-distribution layer; and
the protective shell layer being located above the primary therapeutic layer.

4. The multi-layer heating mat as claimed in claim 3, wherein the heat-shielding layer is made of aluminum foil.

5. The multi-layer heating mat as claimed in claim 3, wherein the semi-rigid material layer is made from pressed cotton.

6. The multi-layer heating mat as claimed in claim 3, wherein the EMF-filtering layer is made from copper.

7. The multi-layer heating mat as claimed in claim 3, wherein the secondary therapeutic layer is made from a material selected from the group consisting of: bamboo, carbon fiber material, and charcoal.

8. The multi-layer heating mat as claimed in claim 1, wherein the plurality of therapeutic stones are made from at least one material selected from the group consisting of: amethyst, jade, and tourmaline.

9. The multi-layer heating mat as claimed in claim 1 comprising:
at least one temperature sensor;
a microcontroller;
the at least one temperature sensor being in thermal communication with the heating layer; and
the at least one temperature sensor being electronically connected to the microcontroller.

10. The multi-layer heating mat as claimed in claim 1 comprising:
a user controller;
the user controller comprising a casing, a microcontroller and a control panel;
the control panel being externally mounted onto the casing;
the microcontroller being mounted within the casing; and
the microcontroller being electronically connected to the control panel, the heating layer and the plurality of PEMF emitters.

11. The multi-layer heating mat as claimed in claim 10 comprising:
the user controller comprising a display device;
the display device being externally mounted into the casing, offset from the control panel, and
the microcontroller being electronically connected to the display device.

12. The multi-layer heating mat as claimed in claim 1 comprising:
the primary therapeutic layer comprising a stone harness.

* * * * *